United States Patent
Liu et al.

(10) Patent No.: US 10,429,318 B2
(45) Date of Patent: Oct. 1, 2019

(54) DETECTION SYSTEM FOR A MULTILAYER FILM AND METHOD THEREOF USING DUAL IMAGE CAPTURE DEVICES FOR CAPTURING FORWARD SCATTERED LIGHT AND BACK SCATTERED LIGHT

(71) Applicant: Industrial Technology Research Institute, Hsin-Chu (TW)

(72) Inventors: Ding-Kun Liu, Hsinchu County (TW); Chia-Hung Cho, Hsinchu (TW)

(73) Assignee: INDUSTRIAL TECHNOLOGY RESEARCH INSTITUTE, Hsin-Chu (TW)

( * ) Notice: Subject to any disclaimer, the term of this patent is extended or adjusted under 35 U.S.C. 154(b) by 160 days.

(21) Appl. No.: 15/846,932

(22) Filed: Dec. 19, 2017

(65) Prior Publication Data
US 2019/0187067 A1    Jun. 20, 2019

(51) Int. Cl.
*G01N 21/94* (2006.01)
*G01N 21/958* (2006.01)
(Continued)

(52) U.S. Cl.
CPC ......... *G01N 21/94* (2013.01); *G01N 21/8806* (2013.01); *G01N 21/958* (2013.01);
(Continued)

(58) Field of Classification Search
CPC .. G01N 21/8806; G01N 21/94; G01N 21/958; G03F 1/84
(Continued)

(56) References Cited

U.S. PATENT DOCUMENTS

| 4,831,274 A | 5/1989 | Kohno et al. |
| 5,717,485 A * | 2/1998 | Ito .......................... G01N 21/94 356/237.1 |

(Continued)

FOREIGN PATENT DOCUMENTS

| CN | 1940540 A | 4/2007 |
| CN | 101506962 | 8/2009 |

(Continued)

OTHER PUBLICATIONS

Taiwan Intellectual Property Office, "Office Action", dated Aug. 28, 2018.
(Continued)

*Primary Examiner* — Que Tan Le
(74) *Attorney, Agent, or Firm* — WPAT, PC

(57) ABSTRACT

A detection system for a multilayer film is provided. The detection system for a multilayer film includes a light source device, a first image capture device, a second image capture device and an image processing device. The light source device projects a pair of parallel incident light to a transparent multilayer film obliquely. The pair of parallel incident light is projected onto the transparent multilayer film for producing and enabling a forward scattered light and a back scattered light to be projected therefrom. The first image capture device captures the back scattered light to produce a first image. The second image capture device captures the forward scattered light to produce a second image. The image processing device is coupled to the first image capture device and the second image capture device. The image processing device is used to compares and detect the differences between the second image and the first image.

17 Claims, 4 Drawing Sheets

(51) Int. Cl.
*G01N 21/88* (2006.01)
*G03F 1/84* (2012.01)
*G01N 21/31* (2006.01)
*G01N 21/84* (2006.01)

(52) U.S. Cl.
CPC ....... *G03F 1/84* (2013.01); *G01N 2021/3181* (2013.01); *G01N 2021/8438* (2013.01)

(58) Field of Classification Search
USPC .......................................... 250/222.2, 559.4
See application file for complete search history.

(56) References Cited

U.S. PATENT DOCUMENTS

| | | |
|---|---|---|
| 6,169,601 B1 | 1/2001 | Eremin et al. |
| 6,836,322 B2 | 12/2004 | Bae |
| 7,760,348 B2 | 7/2010 | Kawahara |
| 8,027,036 B2 | 9/2011 | Kim et al. |
| 2004/0239918 A1 | 12/2004 | Sugihara et al. |
| 2010/0007896 A1 | 1/2010 | Fishbaine |
| 2011/0090492 A1 | 4/2011 | Lemke et al. |

FOREIGN PATENT DOCUMENTS

| | | |
|---|---|---|
| CN | 101988908 | 3/2011 |
| CN | 106323981 A | 1/2017 |
| JP | 2008-261790 A | 10/2008 |
| TW | 200905189 | 2/2009 |
| TW | I443329 | 7/2014 |
| TW | 201732305 A | 9/2017 |

OTHER PUBLICATIONS

Pedro Lilienfeld, "Optical Detection of Particle Contamination on Surfaces: A Review", Jun. 6, 2007, pp. 145-165, Aerosol Science and Technology, Taylor & Francis Group.

* cited by examiner

DETECTION SYSTEM FOR A MULTILAYER FILM AND METHOD THEREOF USING DUAL IMAGE CAPTURE DEVICES FOR CAPTURING FORWARD SCATTERED LIGHT AND BACK SCATTERED LIGHT

TECHNICAL FIELD

The present disclosure relates to a detection system for a multilayer film and method thereof.

BACKGROUND

Generally, organic light emitting diode (OLED) is produced using a manufacturing process of multilayer film. It is noted that the electric properties of the OLED could be adversely affected if there are particle/residual contamination happened in the manufacturing process. Therefore, it is essential to have a cleaning procedure to be performed right after each and every manufacturing step in the process for minimizing the surface particle/residual contamination, and thereby ensuring the quality of the resulting OLED.

For those particle detection systems and methods that are currently available, although there is an advanced detection method of laser-scanning point excitation being developed, it can not be applied as an on-line detection system since its detection speed is still not fast enough.

In addition, since OLED is generally formed as a multilayer film structure that is specifically characterized by not only the thin thickness of the multilayer film structure, but also the thin thickness for each film in the multilayer film structure, it will be difficult to identify the exact defect location in the multilayer film structure by the use of the aforesaid conventional detection methods as any defect in each film of the multilayer film structure will be detected in each detection without means for identifying whether the defect is located at the outer layer or inner layer. Therefore, those conventional detection methods can not be applied as an effective defect analysis in OLED manufacturing and the OLED manufacturing process control as well.

Therefore, it is in need of a detection system for a multilayer film and method thereof capable of overcoming the aforesaid shortcomings.

SUMMARY

The present disclosure provides a detection system for a multilayer film and method thereof, using that the location of any particle can be detected and identified no matter it is located at the inner layer or outer layer in a transparent multilayer film structure by the use of a matching optical system design. That is, the detection system and method of the present disclosure not only can be used for detecting surface defect in a transparent multilayer film structure, but also can further be used as an effective defect analysis and manufacturing process control specifically for the detection on each single layer in the transparent multilayer film structure.

In an embodiment, the present disclosure provides a detection system for a multilayer film, which comprises: a light source device, a first image capture device, a second image capture device and an image processing device. The light source device projects a pair of parallel incident light to a transparent multilayer film obliquely. The pair of parallel incident light is projected onto a transparent multilayer film for producing and enabling a forward scattered light and a back scattered light to be emitted therefrom. The first image capture device captures the back scattered light to produce a first image. The second image capture device captures the forward scattered light to produce a second image. The image processing device is coupled to the first image capture device and the second image capture device. The image processing device is used to compare and detect the differences between the second image and the first image.

In an embodiment, the present disclosure provides a detection method for a multilayer film, which comprises the steps of: projecting a pair of parallel incident light to a transparent multilayer film obliquely for producing and enabling a forward scattered light and a back scattered light to be emitted therefrom; enabling the forward scattered light and the back scattered light to be captured respectively so as to generate a first image and a second image accordingly; and comparing the difference between the second image and the first image.

In the aforesaid detection system and method for a multilayer film, a comparison is enabled to identify the differences between images that are generated by the use of a forward scattered light and a back scattered light as the forward scattered light and the back scattered light is produced by the projection of light onto a transparent multilayer film, and since different films in the transparent multilayer film are formed with different reflection coefficients, the light intensities of the forward scattered light and the back scattered light will be different, and that can be used in the image comparison resulting from the forward scattered light and the back scattered light for determining the location of any particle no matter it is located at the inner layer or outer layer in the transparent multilayer film. That is, the detection system and method of the present disclosure can further be used as an effective defect analysis and manufacturing process control specifically for the detection on each single layer in the transparent multilayer film structure.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

Figure 1:
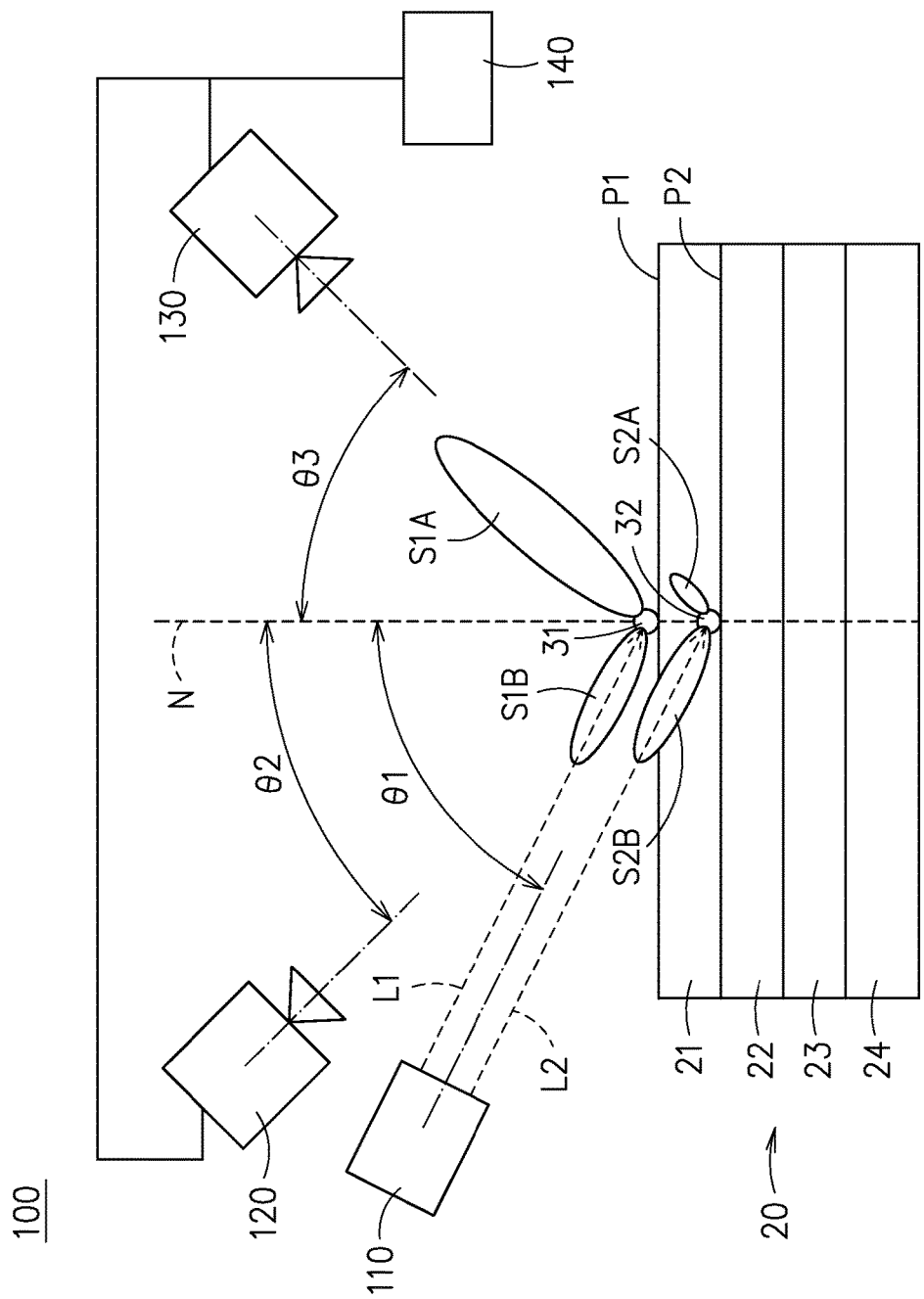
FIG. 1 is a schematic diagram showing a detection system for a multilayer film according to an embodiment of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

FIG. 1 is a schematic diagram showing a detection system for a multilayer film according to an embodiment of the present disclosure. In FIG. 1, a detection system for a multilayer film 100 is provided for detecting a transparent multilayer film 20, in which the transparent multilayer film 20 is composed of a first film 21, a second film 22, a third film 23 and a fourth film 24, and there is a first particle 31 existed on the surface P1 of the first film 21, while there is a second particle 32 existed on the interface P2 of the second film 22.

In this embodiment, the transparent multilayer film 20 is substantially an organic light-emitting diode (OLED) that is specifically characterized not only by the thin thickness for each film in the OLED, but also by that different films in the OLED are formed with different reflection coefficients. In an embodiment, the first film 21 can be a TCO film, the second film 22 can be a $SiO_2$ film, the third film 23 can be a diffuser film and the fourth film 24 can be a PEN film, while different films are formed with different reflection coefficients, e.g. the reflection coefficient of the first film 21 is 1.6 while the reflection coefficient of the second film 22 is 1.5.

In this embodiment, the detection system 100 comprises: a light source device 110, a first image capture device 120, a second image capture device 130 and an image processing device 140. The light source device 110 is used for projecting a parallel pair of a first incident light L1 and a second incident light L2 to a transparent multilayer film 20 obliquely in a manner that the first incident light L1 and the second incident light L2 are projected parallelly in a direction sandwiching a first angle $\theta_1$ with a normal direction N of the transparent multilayer film 20. It is noted that, in the embodiment shown in FIG. 1 the normal direction N is set to be a datum line of 0 degree while defining a positive direction to the left of the normal direction N and a negative direction to the right of the normal direction N. As the light source device 110 of FIG. 1 is disposed at the left to the normal direction N, the degree of the first angle $\theta_1$ is increasing from the normal direction N to the surface P1 of the first film 21, by that the degree of the first angle $\theta_1$ is ranged between 30 degree and 90 degree. In FIG. 1, the first angle $\theta_1$ is set to be 70 degree. However, in another embodiment, as the light source device 110 can be disposed at the right to the normal direction N, consequently the degree of the first angle $\theta_1$ is ranged between −30 degree and −90 degree, that is, it can be a symmetrically opposite angle of −70 degree comparing to that shown in FIG. 1.

In this embodiment, the first incident light L1 is projected onto the first particle 31 on the surface P1 of the first film 21 of the transparent multilayer film 20 for producing and enabling a forward scattered light S1A and a back scattered light SIB to be emitted therefrom in a manner that the forward scattered light S1A is emitting to the front of the projection of the first incident light L1, while the backward scattered light SIB is emitting to the rear of the projection of the first incident light L1 Similarly, the second incident light L2 is projected onto the second particle 32 on the interface P2 of the second film 22 of the transparent multilayer film 20 for producing and enabling a forward scattered light S2A and a back scattered light S2B to be emitted therefrom in a manner that the forward scattered light S2A is emitting to the front of the projection of the second incident light L2, while the backward scattered light S2B is emitting to the rear of the projection of the second incident light L2.

In this embodiment, the detection system 100 is used mainly for detecting particles with diameter larger than 0.3 μm, so that for particles with diameter that is approaching to the wavelength of, the scattering in the system similar to Mie scattering. When the first incident light L1 and the second incident light L2 are projected onto the transparent multilayer film 20 for producing particles of Mie scattering with a diameter larger than 0.3 μm, consequently the light intensity of the forward scattered light is different from that of the corresponding backward scattered light. In an embodiment, the incident light from the light source device 110 is a white light with wavelength of 550 nm, so that the appropriate particle should have a particle diameter larger than 0.5 μm, that is, the diameter of the particle to be detected in the system is adjustable according to the wavelength of the incident light.

In this embodiment, the light intensities of the reflections from different forward scattered light are different according to the different films of different reflection coefficients in the transparent multilayer film 20. In FIG. 1, the reflection coefficient of air is 1, the reflection coefficient of the first film 21 is 1.6, the reflection coefficient of the second film 22 is 1.5, by that the first reflection rate counted from the projection of the first incident light L1 travelling in air to the first film 21 is 14%, and the first reflection rate counted from the projection of the second incident light L2 travelling in air to the second film 22 is 0.1%. Thereby, the light intensity of the forward scattered light S1A resulted from the first incident light L1 is larger than the light intensity of the forward scattered light S2A resulted from the second incident light L2.

In this embodiment, the first image capture device 120 is disposed next to the light source device 110, which can be a camera and is used for capturing the backward scattered light SIB and the backward scattered light S2B, that are resulted respectively from the first incident light L1 and the second incident light L2, so as to be used for generating a first image. It is noted that the first image capture device 120 is located at the left to the normal direction N while causing a second angle $\theta_2$ to be sandwiched between the first image capture device 120 and the normal direction N. Thereby, the second angle $\theta_2$ is ranged between 30 degree and 90 degree, which is different from the first angle $\theta_1$. In the embodiment shown in FIG. 1, the first angle $\theta_1$ is defined to be 70 degree and the second angle $\theta_2$ is defined to be 50 degree. In another embodiment, as the first image capture device 120 is located at the right to the normal direction N, the second angle $\theta_2$ is consequently ranged between −30 degree and −90 degree, that is, it is a symmetrically opposite angle to that shown in FIG. 1, which can be −50 degree.

In the present embodiment, the second image capture device 130 is also disposed next to the light source device 110, which can be a camera and is used for capturing the forward scattered light S1A and the forward scattered light S2A, that are resulted respectively from the first incident light L1 and the second incident light L2, so as to be used for generating a second image. It is noted that the second image capture device 120 is located at the right to the normal direction N. That is, the first image capture device 120 and the second image capture device 130 are located respectively and correspondingly at two opposite sides of the normal direction N. Thereby, there is a third angle $\theta_3$ to be sandwiched between the second image capture device 130 and the normal direction N of the transparent multilayer film 20, whereas the third angle $\theta_3$ is ranged between −30 degree and −90 degree, which is different from the first angle $\theta_1$. In the embodiment shown in FIG. 1, the first angle $\theta_1$ is defined to be 70 degree, the second angle $\theta_2$ is defined to be 50 degree, while the third angle $\theta_3$ is −50 degree, which is a symmetrically opposite angle to the second angle $\theta_2$. In another embodiment, as the second image capture device 130 is located at the left to the normal direction N while the first image capture device 120 is located at the right to the normal direction N, the third angle $\theta_3$ is consequently ranged between 30 degree and 90 degree, that is, it is a symmetrically opposite angle to that shown in FIG. 1, which can be 50 degree. Nevertheless, in further another embodiment when the third angle $\theta_3$ is not defined to be the symmetrically opposite angle to the second angle $\theta_2$, an additional calibration device or process is required for calibrating the images captured by the first image capture device 120 and the second image capture device 130.

In the present embodiment, the image processing device 140 is coupled to the first image capture device 120 and the second image capture device 130 and is used for processing the first image and the second image that are captured respectively from the first image capture device 120 and the second image capture device 130 for comparing and detecting the differences between the second image and the first image. Since different films in the transparent multilayer film 20 are formed with different reflection coefficients, the light intensities of the backward and the forward scattered light emitted from different films will be different, and that can be used by the image processing device 140 in a comparison comparing images formed from different forward and back scattered light of different light intensities for determining the location of any particle no matter it is located at the inner layer or outer layer in the transparent multilayer film.

For instance, in the first image, the backward scattered light S1B and the backward scattered light S2B, that are resulted respectively from the first incident light L1 and the second incident light L2, are used as a basis of reference; and in the second image, as the reflection of the first incident light L1 onto the first film 21 is different from the reflection of the first incident light L1 onto the second film 22 while the reflection coefficient of the first film 21 is larger than that of the second film 22, the light intensity of the forward scattered light S1A will be larger than the light intensity of the forward scattered light S1A, and further the light intensity of the forward scattered light S1A in the second image that are produced by the first incident light L1 will be larger than the light intensity of the backward scattered light S1B in the first image that are also produced by the first incident light L1. Consequently, by comparing the difference between the first image and the second image, the particle 31 can be determined and identified to be located on the surface P1 of the first film 21. Similarly, the light intensity of the forward scattered light S2A in the second image that are produced by the second incident light L2 will be smaller than the light intensity of the backward scattered light S2B in the first image that are also produced by the second incident light L2. Consequently, by comparing the difference between the first image and the second image, the particle 32 can be determined and identified to be located on the interface P2 of the second film 22. Therefore, by comparing two images formed from different forward scattered light S2A of different light intensities, the system and method of the present disclosure is able to determine the location of a particle no matter it is located at the inner layer or outer layer in the transparent multilayer film 20.

Figure 2:
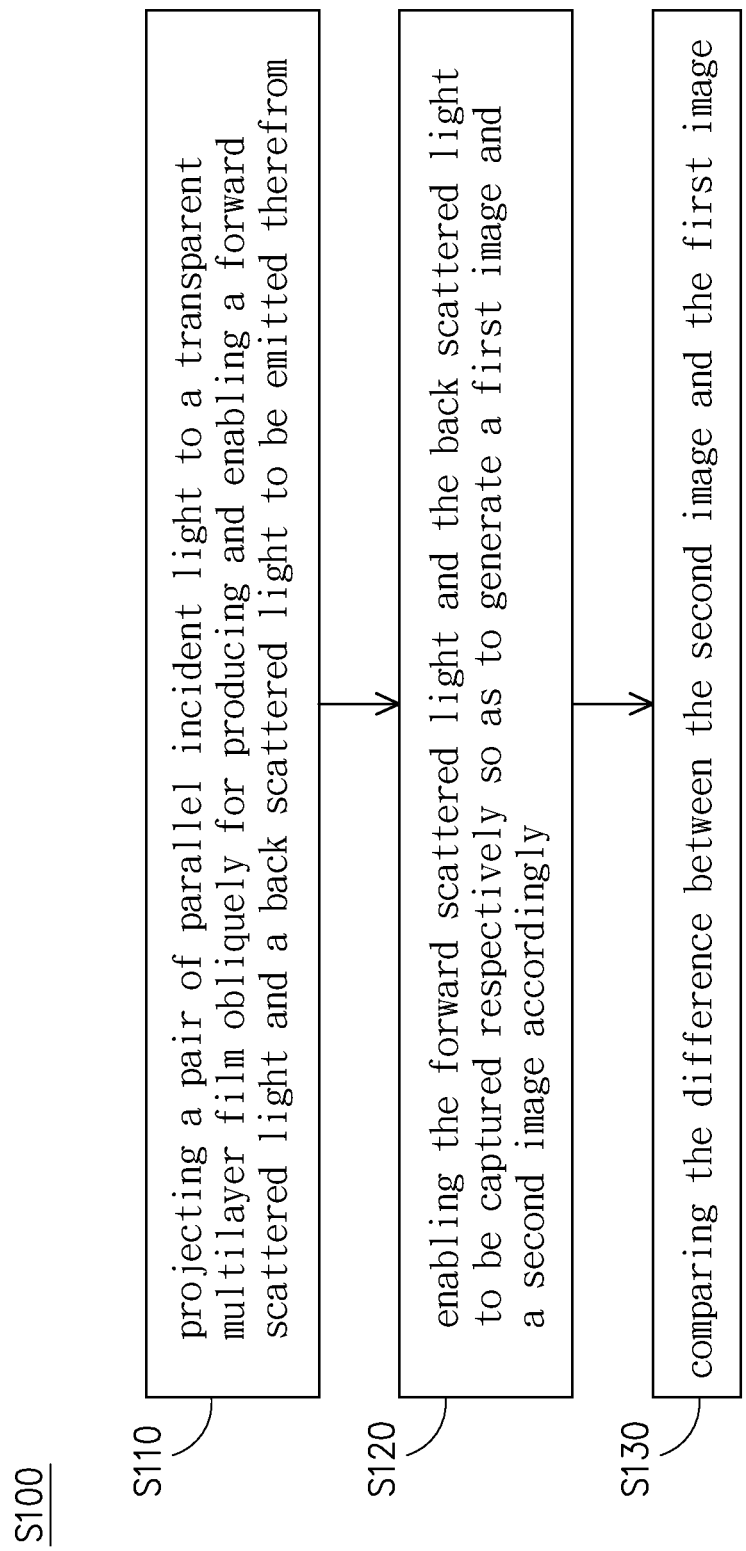
FIG. 2 is a flow chart depicting steps performed in a detection method for a multilayer film of the present disclosure.

FIG. 2 is a flow chart depicting steps performed in a detection method for a multilayer film of the present disclosure. The method S100 of FIG. 2 is adapted for the detection system 100 shown in FIG. 1.

The detection system of FIG. 2 comprises the step S110 to the step S130.

At step S110, a pair of parallel incident light is projected to a transparent multilayer film obliquely for producing and enabling a forward scattered light and a back scattered light to be emitted therefrom. It is noted that the light intensity of the forward scattered light is different from that of the backward scattered light.

Taking the embodiment shown in FIG. 1 for example, the light source device 110 projects a first incident light L1 and a second incident light L2 obliquely to a transparent multilayer film 20. In detail, the light source device 110 projects a first incident light L1 and a second incident light L2 in a direction for causing a first angle $\theta_1$ to be sandwiched between the first incident light L1 and a second incident light L2 and a normal direction N of the transparent multilayer film 20. In an embodiment, the first angle $\theta_1$ is defined to be 70 degree. As the transparent multilayer film 20 contains particles that are larger enough for causing Mie scattering, which has a diameter larger than 0.3 μm, light intensity of the forward scattered light is different from that of the corresponding backward scattered light.

At step S120, the forward scattered light and the back scattered light are captured respectively so as to generate a first image and a second image accordingly.

Taking the embodiment shown in FIG. 1 for example, the first image capture device 120 and the second image capture device 130 are located respectively and correspondingly at two opposite sides of the normal direction N for enabling a second angle $\theta_2$ to be sandwiched between the first image capture device 120 and the normal direction N of the transparent multilayer film 20 and also enabling a third angle $\theta_3$ to be sandwiched between the second image capture device 130 and the normal direction N of the transparent multilayer film 20. Thereby, the second angle $\theta_2$ is different from the first angle $\theta_1$, and also the third angle $\theta_3$ is different from the first angle $\theta_1$ while enabling the third angle $\theta_3$ to be a symmetrically opposite angle to the second angle $\theta_2$. In an embodiment, the first angle $\theta_1$ is 70 degree, the second angle $\theta_2$ is 50, while third angle $\theta_3$ is −50 degree. By disposing the first image capture device 120 and the second image capture device 130 respectively at an angle different from the disposition angle of the projection direction of the light source device 110, the first image capture device 120 and the second image capture device 130 can be prevented from receiving unwanted reflection.

Using the aforesaid configuration, the first image capture device 120 is used for capturing the backward scattered light S1B and the backward scattered light S2B, that are resulted respectively from the first incident light L1 and the second incident light L2, so as to be used for producing a first image, and similarly the second image capture device 130 is used for capturing the forward scattered light S1A and the forward scattered light S2A, that are resulted respectively from the first incident light L1 and the second incident light L2, so as to be used for producing a second image.

Thereafter, the flow proceeds to step S130. At step S130, the second image is compared with the first image. For further detailed description, please refer to FIG. 3, FIG. 4A and FIG. 4B.

Figure 4B:
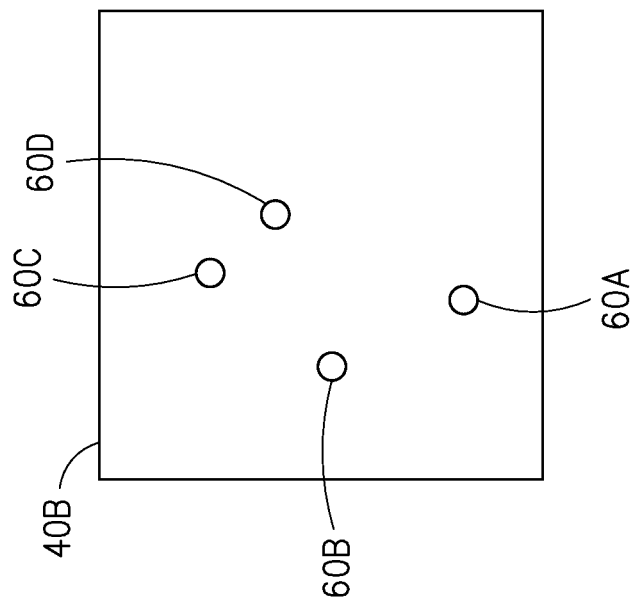
FIG. 4B is a schematic diagram showing a second image according to an embodiment of the present disclosure.
Figure 4A:
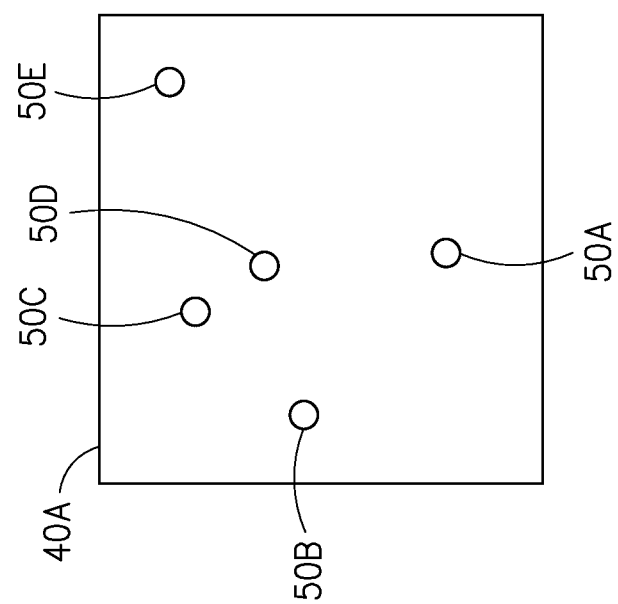
FIG. 4A is a schematic diagram showing a first image according to an embodiment of the present disclosure.

At step S132, the first image and the second image are detected respectively for determining whether there are particles being generated on the first image and the second image. As shown in FIG. 4A, there is a first image 40A being produced by the first image capture device 120 using the backward scattered light S1B and the backward scattered light S2B, that are resulted respectively from the first incident light L1 and the second incident light L2. In the first image 40A, there are five particles 50A~50E being detected. In addition, there is a second image 40B being produced by the second image capture device 130 using the forward scattered light S1A and the forward scattered light S2A, that are resulted respectively from the first incident light L1 and the second incident light L2. In the second image 40B, there are four particles 60A~60D being detected.

Figure 3:
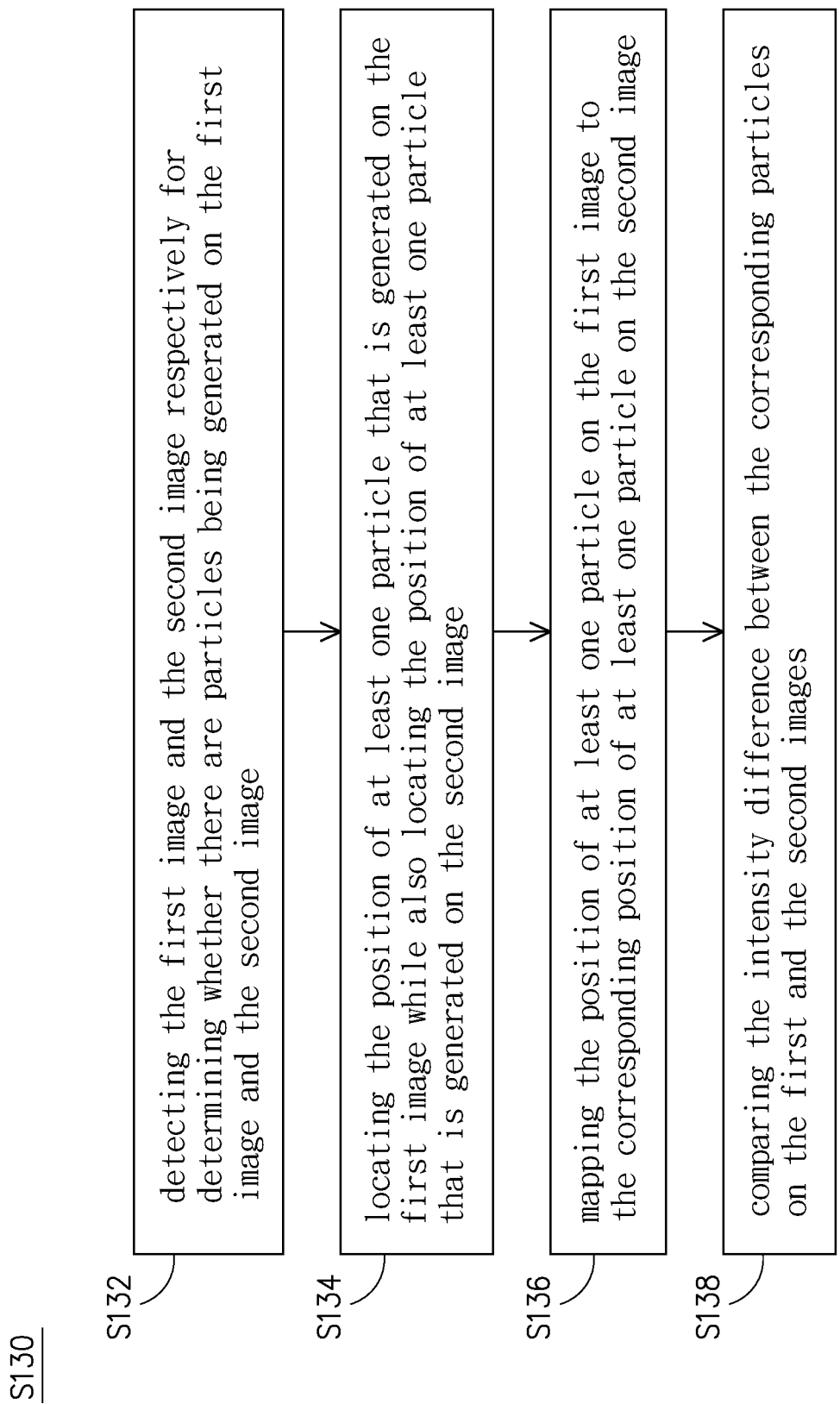
FIG. 3 is a flow chart depicting steps for comparing the second image to the first image of FIG. 2.

At step 134, with reference to FIG. 3, the positions of the five particles 50A~50E on the first image 40A are searched and located while the positions of the four particles 60A~60D on the second image 40B are also searched and located.

At step S136, the position of the five particles on the first image 40A are mapped to the corresponding position of the four particles 60A~60D on the second image 40B. In the present embodiment, an image registration method can be used for determining and identifying which particles in the second image 40B is most similar to the one particle selected from the first image 40A. In an embodiment, the particle 50A of the first image 40A is mapped with the particle 60A of the second image 40B, the particle 50B of the first image 40A is mapped with the particle 60B of the second image 40B, the particle 50C of the first image 40A is mapped with the particle 60C of the second image 40B, and the particle 50D of the first image 40A is mapped with the particle 60D of the second image 40B, but there is no particle in the second image 40B that can map with the particle 50E in the first image 40A.

At step S138, the intensity difference between the corresponding particles on the first and the second images are compared. In the aforesaid embodiment as there is no particle in the second image 40B that can map with the particle 50E in the first image 40A, the particle 50E can be identified to be a particle existed in the inner layer of the transparent multilayer film 20. In another embodiment as the particle 50C of the first image 40A is mapped with the particle 60C of the second image 40B and as the light intensity of the particle 60C is smaller than the light intensity of the particle 50C, the particle 60C, that is corresponding to the particle 50C, is identified to be a particle existed in the inner layer of the transparent multilayer film 20. In another embodiment as the particle 50A of the first image 40A is mapped with the particle 60A of the second image 40B and as the light intensity of the particle 60AC is larger than the light intensity of the particle 50A, the particle 60A, that is corresponding to the particle 50A, is identified to be a particle existed on the surface P1 of the first film 21 in the transparent multilayer film 20. That is, by comparing the light intensity difference between two corresponding particles, the location of the particles can be determined no matter it is located at the inner layer or outer layer in the transparent multilayer film.

To sum up, in the aforesaid detection system and method for a multilayer film, a comparison is enabled to identify the differences between images that are generated by the use of a forward scattered light and a back scattered light as the forward scattered light and the back scattered light is produced by the projection of light onto a transparent multilayer film, and since different films in the transparent multilayer film are formed with different reflection coefficients, the light intensities of the forward scattered light and the back scattered light will be different, and that can be used in the image comparison resulting from the forward scattered light and the back scattered light for determining the location of any particle no matter it is located at the inner layer or outer layer in the transparent multilayer film. That is, the detection system and method of the present disclosure can further be used as an effective defect analysis and manufacturing process control specifically for the detection on each single layer in the transparent multilayer film structure.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A detection system for a multilayer film, comprising:
a light source device, projecting a pair of parallel incident light to a transparent multilayer film obliquely for producing and enabling a forward scattered light and a back scattered light to be emitted therefrom;
a first image capture device, capturing the back scattered light to produce a first image;
a second image capture device, capturing the forward scattered light to produce a second image; and
an image processing device, coupling to the first image capture device and the second image capture device for comparing and detecting the differences between the second image and the first image.

2. The detection system of claim 1, wherein the pair of parallel incident light is projected in a direction sandwiching a first angle with a normal direction of the transparent multilayer film.

3. The detection system of claim 2, wherein the first angle is ranged between −30 degree and −90 degree.

4. The detection system of claim 2, wherein the first angle is ranged between 30 degree and 90 degree.

5. The detection system of claim 2, wherein the first image capture device is disposed in a direction sandwiching a second angle with the normal direction of the transparent multilayer film in a manner that the second angle and the first angle are different from each other; and the second image capture device is disposed in a direction sandwiching a third angle with the normal direction of the transparent multilayer film in a manner that the third angle and the first angle are different from each other.

6. The detection system of claim 5, wherein the third angle is a symmetrically opposite angle to the second angle.

7. The detection system of claim 5, wherein the second angle is ranged between 30 degree and 90 degree, and the third angle is ranged between −30 degree and −90 degree.

8. The detection system of claim 5, wherein the second angle is ranged between −30 degree and −90 degree, and the third angle is ranged between 30 degree and 90 degree.

9. The detection system of claim 1, wherein the forward scattered light is emitting to the front of the projection of the pair of parallel incident light, while the backward scattered light is emitting to the rear of the projection of the pair of parallel incident light.

10. The detection system of claim 1, wherein the light intensity of the forward scattered light is different from that of the corresponding backward scattered light.

11. The detection system of claim 1, wherein the image processing device is used for comparing and detecting the light intensity difference between forward scattered light of the second image and the backward scattered light of the first image.

12. A detection method for a multilayer film, comprising:
projecting a pair of parallel incident light to a transparent multilayer film obliquely for producing and enabling a forward scattered light and a back scattered light to be emitted therefrom;
enabling the forward scattered light and the back scattered light to be captured respectively so as to generate a first image and a second image accordingly; and
comparing the difference between the second image and the first image.

13. The detection method of claim 12, further comprising:
providing a light source device for projecting the pair of parallel incident light to the transparent multilayer film in a direction sandwiching a first angle to a normal direction of the transparent multilayer film.

14. The detection method of claim 12, further comprising:
providing a first image capture device and a second image capture device to be disposed in a manner that the first image capture device is disposed in a direction sandwiching a second angle with the normal direction of the transparent multilayer while enabling the second angle to be different from the first angle, and the second image capture device is disposed in a direction sandwiching a third angle with the normal direction of the transparent multilayer film while enabling the third angle to be different from the first angle.

15. The detection method of claim 14, wherein the third angle is a symmetrically opposite angle to the second angle.

16. The detection method of claim 12, wherein the comparing of the difference between the second image and the first image further comprising:
detecting the first image and the second image respectively for determining whether there are particles being generated on the first image and the second image;
locating the position of at least one particle that is generated on the first image while also locating the position of at least one particle that is generated on the second image;
mapping the position of at least one particle on the first image to the corresponding position of at least one particle on the second image; and
comparing the intensity difference between the corresponding particles on the first and the second images.

17. The detection method of claim 12, wherein the light intensity of the forward scattered light is different from that of the corresponding backward scattered light.

* * * * *